(12) United States Patent
Dwyer et al.

(10) Patent No.: US 6,395,017 B1
(45) Date of Patent: May 28, 2002

(54) ENDOPROSTHESIS DELIVERY CATHETER WITH SEQUENTIAL STAGE CONTROL

(75) Inventors: Clifford J. Dwyer, Wilmington, MA (US); Timothy Robinson, Sandown, NH (US)

(73) Assignee: C. R. Bard, Inc., Murray Hill, NJ (US)

( * ) Notice: Subject to any disclaimer, the term of this patent is extended or adjusted under 35 U.S.C. 154(b) by 499 days.

(21) Appl. No.: 08/751,087

(22) Filed: Nov. 15, 1996

(51) Int. Cl.⁷ .................................................. A61F 2/06
(52) U.S. Cl. ..................................... 623/1.11; 623/1.23
(58) Field of Search .................. 606/108, 191–200; 623/1.11–1.25

(56) References Cited

U.S. PATENT DOCUMENTS

| | | | | |
|---|---|---|---|---|
| 5,250,071 A | * | 10/1993 | Palermo | 606/108 |
| 5,391,172 A | * | 2/1995 | Williams et al. | 606/198 |
| 5,474,563 A | * | 12/1995 | Myler et al. | 606/108 |
| 5,484,444 A | * | 1/1996 | Braunschweiler et al. | 606/108 |
| 5,562,698 A | * | 10/1996 | Parker | 606/198 |
| 5,601,600 A | * | 2/1997 | Ton | 606/198 |
| 5,702,419 A | * | 12/1997 | Berry et al. | 606/108 |
| 5,709,703 A | * | 1/1998 | Lukic et al. | 606/198 |
| 5,733,325 A | * | 3/1998 | Robinson et al. | 623/1 |

* cited by examiner

*Primary Examiner*—Glenn K. Dawson
(74) *Attorney, Agent, or Firm*—Kirkpatrick & Lockhart LLP

(57) ABSTRACT

A delivery device for intraluminally positioning and controllably releasing a vascular prosthesis includes an elongate delivery sheath and a control handle at the proximal end of the device. The handle has components movable and arranged to define at least three relative positions including (1) an implant capture position in which the sheath fully encloses and contains the implant, (2) an intermediate position in which the implant is partially deployed but in which the trailing end of the implant remains attached to the delivery device, and (3) a release position in which the implant has been freed from the delivery device and fully released within the blood vessel. The movable parts of the handle include a shifting mechanism that must be operated deliberately through a detent by the physician to enable the handle to be manipulated from one position to the other.

31 Claims, 9 Drawing Sheets

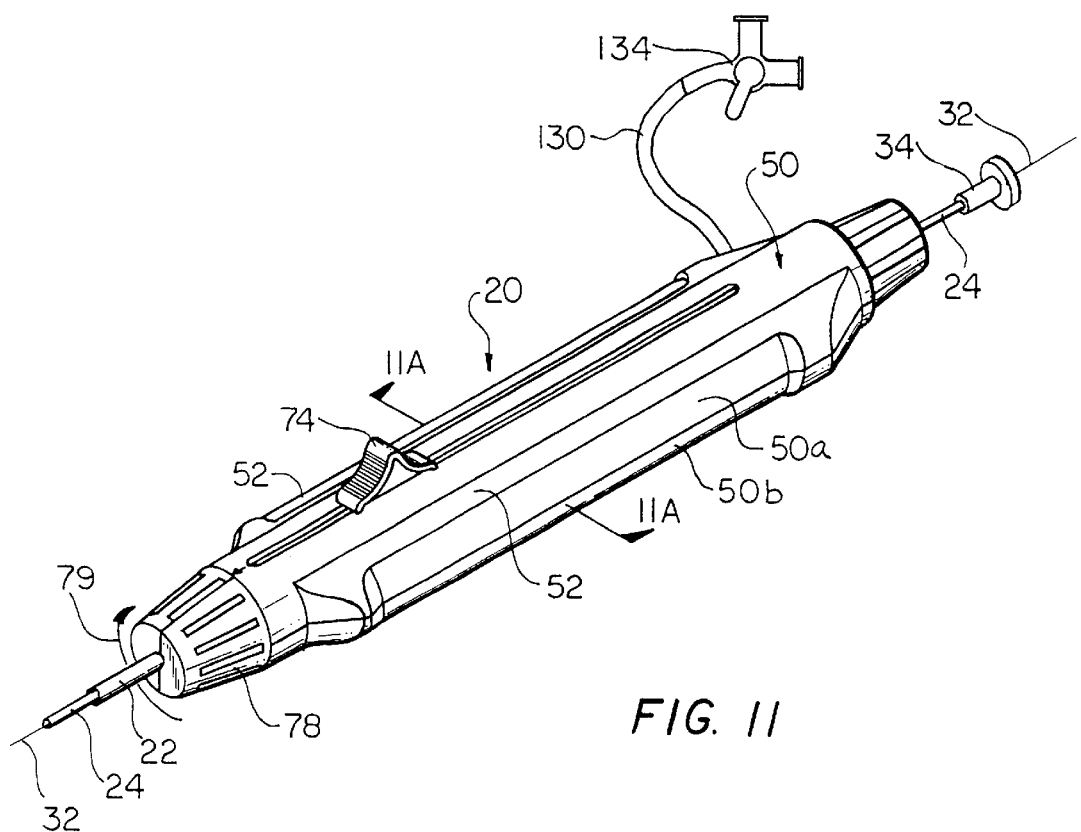
FIG. 11
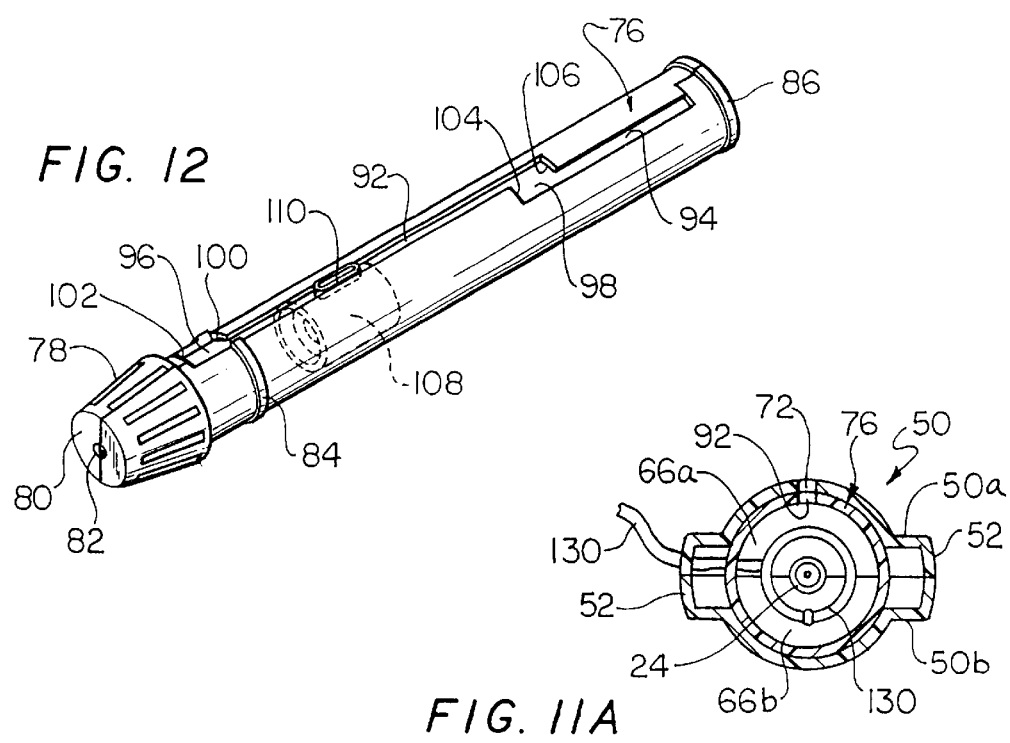
FIG. 12
FIG. 11A

ENDOPROSTHESIS DELIVERY CATHETER WITH SEQUENTIAL STAGE CONTROL

FIELD OF THE INVENTION

The invention relates to delivery catheters for delivering and deploying an endoluminal implant to a remote site within a body lumen.

BACKGROUND OF THE INVENTION

It has long been accepted medical practice to treat a variety of vascular disorders in a surgical procedure that involves surgical exposure of the portion of the patient's vascular system to be treated and placement of a vascular graft at that site. In order to reduce the risks inherent in such surgery, various devices and techniques for advancing and deploying a vascular graft without requiring a full surgical procedure have been under development. Among those techniques is to provide a tubular implant assembly that can be radially contracted to a low profile (small effective cross-sectional diameter) and loaded into a delivery catheter to enable the catheter to be advanced through the patient's vasculature to deliver and deploy the implant at its intended site of placement. When located at the intended deployment site, the catheter is operated to eject the implant so that it can deploy to its radially expanded configuration in engagement with the inner surface of the blood vessel.

Among the difficulties presented in such endoluminal placement of an implant is that the implant and catheter are not directly visible to the physician. Therefore, in order for the physician to determine the location of the catheter and the implant, as well as its position within the blood vessel, fluoroscopic techniques are used. Radiopaque elements may be provided on one or both of the implant and delivery catheter. Additionally, radiopaque contrast liquid may be injected into the blood vessel. However, even if the predeployment position of the implant appears to be satisfactory, further manipulation of the delivery catheter in order to deploy the implant, may result in shifting of the graft and misplacement either as to its location, orientation or both.

European patent applications Ser. No. 94116805.6 filed Nov. 10, 1994 (Publication No. 0657147) and Ser. No. 95114543.2 filed Sep. 15, 1995 (Publication No. 0701800A1) describe a recapturable prosthetic implant system that includes an implant and a delivery device in which a substantial portion of the implant may be ejected from the delivery device sufficiently to enable determination whether the implant is in its proper location, orientation and of the correct size. The implant and delivery system are configured to enable the implant to be retracted into the delivery device in the event that the location or orientation is improper. With the implant recaptured, the delivery device can be manipulated into the proper position. The implant then can be partially deployed and its position and orientation again determined. When the implant is located as desired, the delivery device is operated to fully release the implant. The construction of the implant is such that it will remain in the deployed position within the blood vessel.

The delivery device is in the form of a catheter having an elongate tubular sheath arranged to contain the implant in its low profile within the distal end of the sheath. The device also includes an elongate positioning member that extends through the sheath and implant and engages with the trailing end of the implant. The positioning member has a hollow lumen adapted to receive a guidewire so that the delivery device can be advanced into and navigated through the patient's vascular system in an over-the-wire technique.

When the delivery system and implant have been advanced to the intended site of deployment, the positioning member is held stationary while the sheath is withdrawn. As the sheath is withdrawn, the implant is progressively exposed and expands radially toward engagement with the wall of the blood vessel.

An end of the implant remains attached to the positioning member and remains so until the sheath has been withdrawn past the connection of the implant, at which point the implant is released. At any time before the point of release, the sheath can be readvanced over the implant to recapture the implant.

The implant, for example, may include a tubular synthetic graft having leading and trailing ends and a resilient, self-expanding anchor assembly, connected to the graft, that is compressible to a low profile and can expand resiliently to an enlarged diameter. The anchor assembly may include an anchor at each end. Each anchor may be formed generally in the configuration of a continuous zigzag wire arranged in a tubular configuration. Portions of the anchors at the opposite ends of the implant are connected to two or more longitudinal struts. The anchors may be provided with one or more radially outward protruding hooks adapted to engage the blood vessel wall under the influence of the resilient anchor to enhance the resistance of the anchor to migration once the graft has been released from the delivery device.

There is some risk that as the deployment of the device approaches its completion, there may be premature accidental release of the implant. It would be desirable, therefore, to provide a means and method by which such accidental premature release could be prevented.

SUMMARY OF THE INVENTION

The delivery catheter is provided with a control handle at its proximal end. The handle has movable components connected respectively to the sheath and the positioning member to control their relative longitudinal movement and position. The handle components are arranged to define at least three relative positions of the sheath and positioning member including (1) an implant capture position in which the sheath fully encloses and contains the implant, (2) a further stage of the implant capture state in which the implant is partially deployed from the sheath but in which the trailing end of the implant remains attached to the delivery device, and (3) a release configuration in which the implant has been ejected from the sheath sufficiently to enable it to be freed from the sheath and fully released within the blood vessel. In the illustrative embodiment, the movable parts of the handle include a shifting mechanism that must be operated deliberately by the physician to enable the handle to be manipulated from one position to the other. Thus, the physician can be confident that the implant will not be deployed prematurely and that it will be released only when the physician is satisfied with its placement and position. The device is ergonomic and can be operated entirely by feel. Thus, the physician is relieved of continuous visual checking of the relative positions of the sheath and the positioning member.

It is among the general objects of the invention to provide an improved delivery device and method for an endoluminal implant that enables the implant to be deployed in partial progressive stages.

Another object of the invention is to provide an improved delivery device for an endoluminal implant in which inadvertent release of the implant is avoided.

A further object of the invention is to provide an improved delivery device for an endoluminal implant that facilitates recapture of the implant.

A further object of the invention is to provide a device of the type described that can be operated substantially by feel and without requiring that the physician divert attention from the other aspects of the procedure.

DESCRIPTION OF THE DRAWINGS

The foregoing and other objects and advantages of the invention will be appreciated more fully from the following further description, with reference to the accompanying drawings wherein:

FIG. 11 is an illustration of the control handle of the deployment device;

FIG. 11A is a sectional illustration through the control handle as seen along the line 11A—11A of FIG. 11;

FIG. 12 is an illustration of the internal shift tube of the handle;

DESCRIPTION OF THE PREFERRED EMBODIMENT

Figure 1:
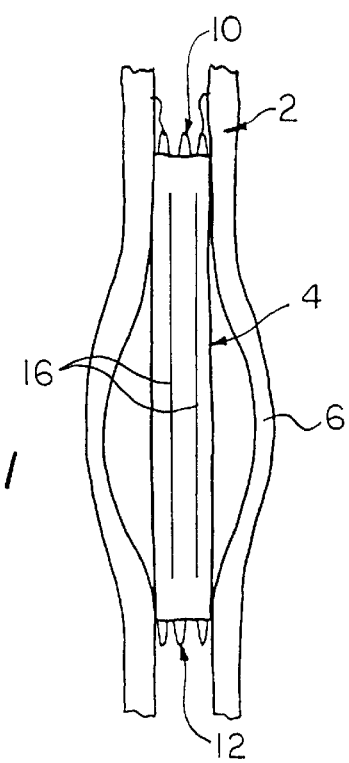
FIG. 1 is a diagrammatic illustration of a blood vessel having an aneurysm with an endoluminal tubular implant disposed within the aneurysm to reinforce the blood vessel.

FIG. 1 illustrates, diagrammatically, a blood vessel, such as an artery 2, in which a tubular implant assembly 4 has been placed to serve as a reinforcing liner in the region of an aneurysm 6. The aneurysm 6 defines a weakened region of the wall of the artery and may be susceptible to rupture and consequent hemorrhaging under the influence of arterial blood pressure. The implant assembly 4 is adapted to be placed endoluminally, as by radially contracting it within the sheath of a delivery catheter, inserting the catheter into a blood vessel to access the aneurysm, positioning the device within the aneurysm and then releasing the implant assembly 4 into engagement with healthy arterial tissue beyond each end of the aneurysm.

In the following description, a direction along which the delivery device is advanced will be referred to as "leading" or "forward" and the opposite direction will be referred to as "trailing" or "rearward". Thus, the implant assembly 4 may be considered as having a leading end 3 and a trailing end 5. When the implant assembly 4 has been advanced into and through the blood vessel from a downstream location to an upstream deployment location, the leading end of the implant assembly 4 also may be considered as being "upstream" and the trailing end as "downstream".

Figure 2:
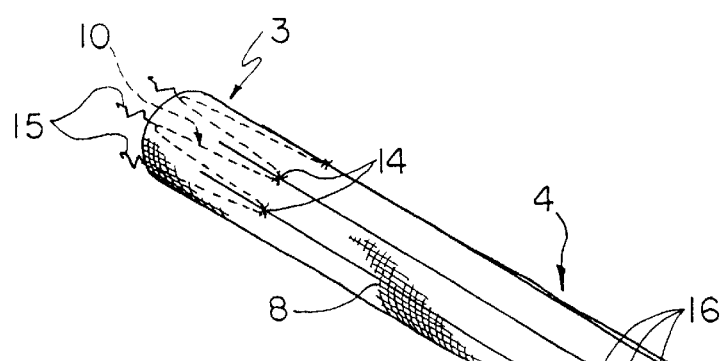
FIG. 2 is an illustration of an embodiment of a single tubular implant that can be placed with the delivery device.

FIG. 2 illustrates, generally, an exemplary implant assembly 4 that may be used in the practice of the present invention. The assembly includes an elongate flexible tubular graft 8 that may be of woven or other conventional vascular graft construction. The implant includes an anchor assembly that is connected to the graft 8 to maintain the ends of the graft 8 open as well as to facilitate recapture of the implant assembly 4 within the delivery device to enable repositioning or withdrawal of the graft. The anchor assembly may include a variety of configurations including that illustrated in FIG. 2 having a pair of resiliently expandable anchors including a leading anchor 10 and a trailing anchor 12. Each of the anchors 10, 12 may be formed from a suitable wire such as MP35N alloy in a zigzag configuration that defines a circumferential configuration. The anchors 10, 12 may be attached to the graft 8 by a combination of sutures 14 and by passing portions of the wire from which the anchors 10, 12 are made through openings or interstices in the fabric graft.

FIG. 2 illustrates a tubular implant in a relaxed configuration in which the anchors 10, 12 have expanded to the extent permitted by the dimensions of the graft 8. Preferably the anchor and graft are selected with respect to the diameter of the body lumen in which they are to be placed so as they are expanded they will firmly and securely engage the lumen of the vessel. The implant 4 can be contracted radially to a compact, low profile configuration insertable into the distal end of the delivery device, as described below.

Figure 2A:
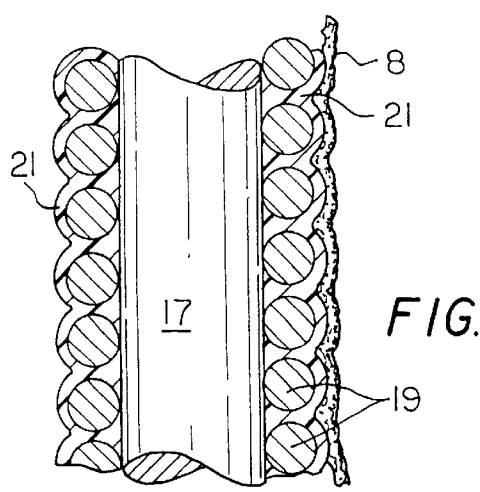
FIG. 2A is a greatly enlarged longitudinal section of a portion of a strut of the implant assembly.

The implant assembly 4 also includes a connection between the leading and trailing anchors 10, 12 in the form of elongate struts 16. The struts may be attached to the outer surface of the graft 8 by the sutures 14 that also secure the struts at their junctions with the anchors 10, 12 and the graft 8. The struts 16 also may be attached above their lengths to the exterior surface of the graft 8 by heat bonding. FIG. 2A shows, in greatly enlarged detail, the construction for the struts 16. The struts preferably include an inner core wire 17 surrounded by a helical coil 19 wrapped tightly about the core wire 17. The coil is wrapped in a thin tube of thermoplastic polymeric material 21. The polymeric layer may comprise polypropylene, applied as a tube about the coil 19 and then heated sufficiently to enable the polypropylene to begin to melt and flow into close intimacy with the turns of the coil 19. The polymeric layer may be applied, for example, in the form of tubing. The polymeric layer 21 may be formed from the same or a different polymeric material from which the graft 8 is formed. The strut may be attached firmly to the graft by heat bonding the polymeric covering directly to the graft material, as suggested in FIG. 2A. With this arrangement, the struts may be attached securely along their full lengths to the graft 8 to provide full support for the graft 8. The core wire 17 and wire from which the coil 19 is formed may be formed from MP35N alloy. The construction of the struts provides enhanced rigidity after the device is assembled while at the same time allowing the device to collapse to a low profile. A strut so constructed is considered to have sufficient radiopacity to permit adequate X-ray or fluoroscopic visualization of the struts when implanted in the abdominal aorta. Should it be desired to add a radiopaque filler material to the polymeric material 21, that may enhance the radiopacity.

As shown in FIG. 2 the leading anchor 10 preferably is provided with hooks 15 arranged to project radially outwardly to engage the healthy tissue of the vessel into which the implant is placed. A variety of hook configurations may be employed, including those described in the above-referenced patent applications. Reference is made to the disclosures in the above-referenced European patent applications, the disclosures of which are incorporated herein in their entireties, for additional details and embodiments of such implant assemblies.

Figure 3:
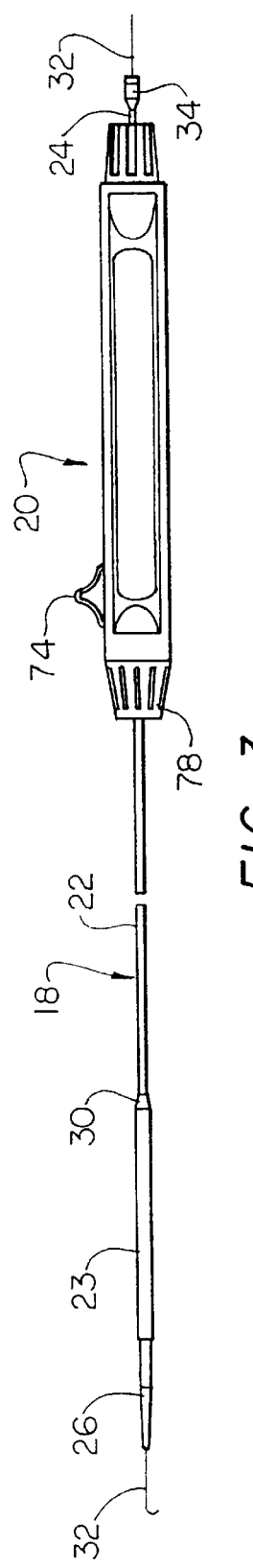
FIG. 3 is a side illustration of the delivery device for the implant assembly.
Figure 4:
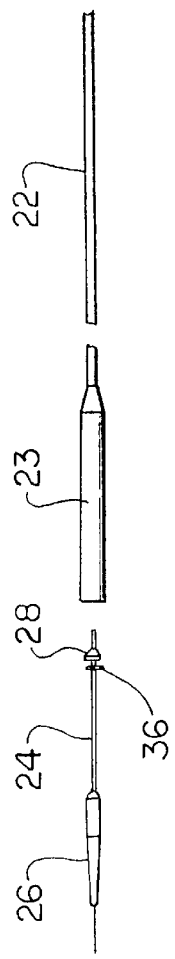
FIG. 4 is a fragmented illustration of the distal region of the delivery device.

The delivery device is shown in FIG. 3 and includes an elongate flexible shaft 18 and a control handle 20. The shaft includes an elongate flexible sheath 22 (FIGS. 4, 6) formed from a suitable polymeric material. The leading end of the sheath 22 may be formed to include an enlarged diameter pod 23 adapted to receive the compacted, low profile implant assembly 4. The distal end of the pod 23 may be provided with a radiopaque marker band 25 (FIG. 6). The shaft also includes a positioning tube 24 that extends through the sheath 22 and has, at its leading end, a flexible tapered dilator 26. The rear portion of the dilator 26 is dimensioned to be engaged with the distal end of the pod (FIG. 5) to close the open end of the pod during advancement of the delivery device as well as after the implant has been deployed to maintain the pod closed during withdrawal of the delivery device. A stay 28 is secured to the positioning tube 24 rearward of the dilator 26. The trailing end of the dilator 26 is dimensioned to be received within the lumen at the leading end of the sheath 22. The positioning tube 24 is longer than the combined length of the sheath 22 and the control handle 20 so that, when assembled, the trailing end of the positioning tube 24 can protrude rearwardly from the control handle 20 while the dilator 26 is forward of the end of the sheath. The positioning tube 24 is open at its leading and trailing ends and is adapted to receive a guidewire 32 through the lumen of the tube 24. The trailing end of the positioning tube 24 preferably is provided with a luer fitting 34. The stay 28 has openings to enable fluid to pass beyond the stay.

Figure 5:
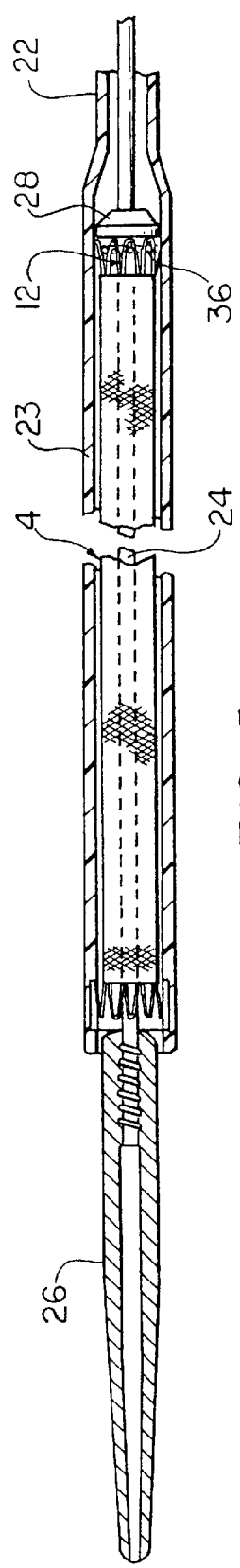
FIG. 5 is an enlarged sectional illustration of the distal region of the delivery device loaded with the implant assembly and in readiness for insertion into a patient.
Figure 6:
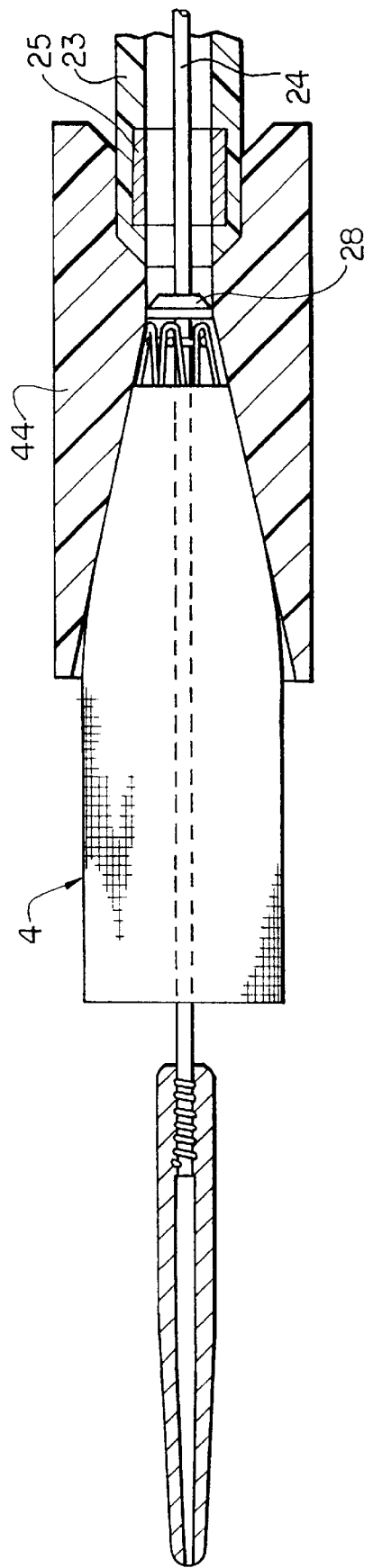
FIG. 6 is a diagrammatic illustration of the manner in which the implant may be loaded into the distal end of the delivery device.
Figure 7:
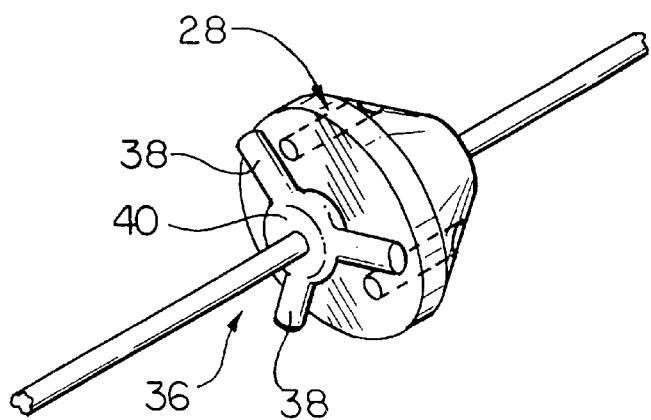
FIG. 7 is an enlarged illustration of an embodiment of a stay and implant retention device adapted to securely engage the trailing end of the implant assembly.
Figure 8:
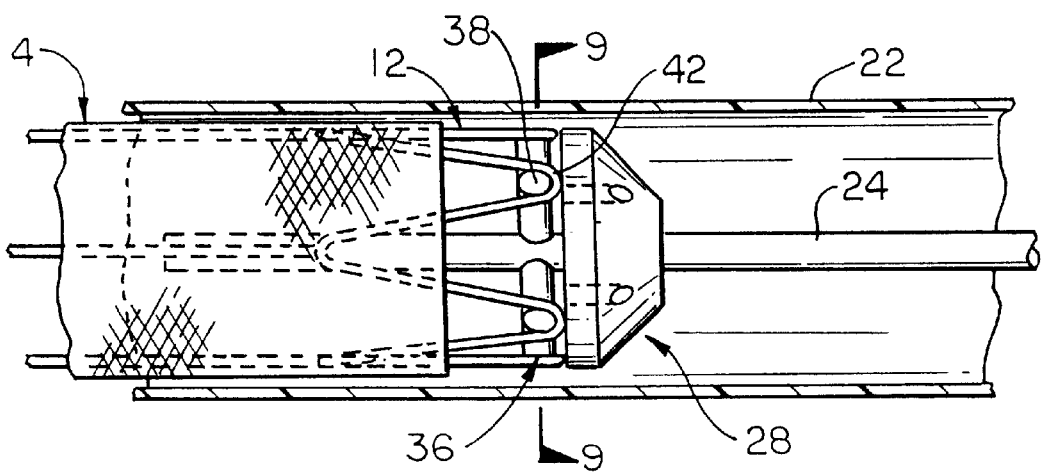
FIG. 8 is a sectional illustration of the trailing end of an implant assembly contained within the delivery device and in engagement with the stay and retention device.
Figure 9:
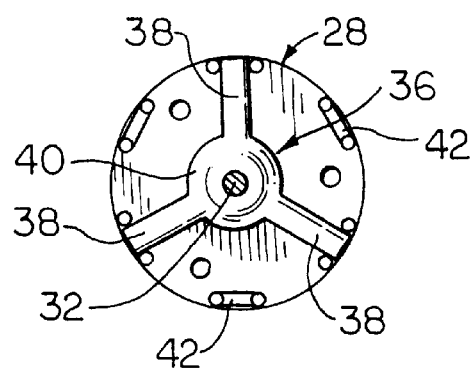
FIG. 9 is an illustration of the retention device as seen along the line 9—9 of FIG. 8.

FIG. 5 illustrates, in longitudinal cross-section, the leading end of the device with the compacted implant assembly 4 contained within the pod 23 of the sheath 22. The implant 4 will be disposed about a portion of the positioning tube 24. The trailing anchor 12 will be in abutting engagement with the stay 28 when the device is so loaded. The stay 28 engages the trailing anchor 12 to maintain the position of the implant assembly 4 as the sheath 22 is withdrawn. The stay 28 functions in conjunction with an anchor retainer 36 disposed just forwardly of the stay 28 (FIGS. 7 and 8). The stay 28 and anchor retainer 36 may be considered to comprise an implant retainer. The anchor retainer 36 may take the form of one or more radially extending spokes 38 attached to a central hub 40. The anchor retainer 36 may be mounted on the positioning tube 24 or may be formed as an integral part of the stay 28. As can be seen most clearly in FIG. 8, when the implant assembly 4 is engaged with the delivery device, the spokes 38 of the anchor retainer 36 engages the trailing ends of the anchor 12 within the region defined by the bends 42 (FIGS. 8 and 9). Cooperation of the trailing anchor 12 with the stay 28 and anchor retainer 36 effectively secure the implant assembly 4 to the positioning tube 24 to prevent longitudinal movement between the two. The implant assembly, therefore, can be maintained in position by maintaining the position of the positioning tube 24 while permitting the sheath to be withdrawn or advanced as desired.

FIG. 6 illustrates, diagrammatically, the configuration of the system when the implant assembly 4 is loaded into the delivery device. The positioning tube 24 is extended through the sheath 22 with its leading end extending beyond the distal end of the pod 23 so that the stay 28 and retention device 36 extend slightly beyond the leading end of the pod 23. A loading funnel 44 is placed about the positioning tube 24 with the trailing end of the funnel communicating with the leading end of the pod 23. The implant assembly 4 is placed over the leading end of the positioning tube 24 such that the trailing bends 42 of the trailing anchor 12 are disposed against the stay 28. The implant assembly is pushed into the funnel 44 to compress the trailing end of the anchor 12 and to move the anchor 12, stay 28 and retention device 36 into the leading end of the pod. As the implant assembly passes through the funnel 44 it is progressively constricted to a low profile about the positioning tube 24 and is withdrawn into the pod 23 in a compressed, low profile configuration. The loading continues until the trailing end of the dilator 26 has been brought into engagement with the leading end of the pod 23 (FIG. 5). Preferably, the dilator 26 and pod 23 are configured to present a relatively smooth transition to minimize trauma as the device is advanced into and through the patient's vasculature. So loaded, the implant and its delivery device are in readiness to be inserted and advanced into the patient's vasculature to deploy and release the device.

The device can be inserted into the patient's vasculature with the aid of a guidewire 32. The guidewire may be placed in the blood vessel separately in a preliminary procedure. The delivery device then is advanced into the patient's blood vessel, for example, as through the femoral artery, when placing an implant to treat an abdominal aortic aneurysm. The guidewire may be advanced independently toward and through the region to be treated. The delivery catheter then may be advanced over the guidewire until the implant assembly is in its intended location in the blood vessel. In the case of an abdominal aortic aneurysm, the device would be located so that the leading anchor 10 is located upstream of the region of the aneurysm such that the implant, when deployed, can pass through the aneurysm thereby lining the artery. With the delivery device so placed, the position of the positioning tube 24 is maintained while the sheath 22 is withdrawn. The stationary stay 28 maintains engagement with the trailing end of the anchor 12 in the manner described above, thereby preventing rearward movement of the implant assembly while the sheath is withdrawn. As the sheath is progressively withdrawn and the trailing anchor 12 emerges from the distal end of the pod 23, the anchor expands into engagement with the inner luminal surface of the blood vessel while simultaneously expanding the distal end of the graft.

The implants are characterized in their ability to be removed from or repositioned within the patient prior to completion of the deployment process. In particular, as long as a trailing portion of the implant is maintained within the pod 23, the deployment process can be reversed to recapture the implant and reposition or remove it. As discussed above, progressive withdrawal of the sheath 22 and pod 23 exposes progressive lengths of the implant to enable the implant to expand into contact with the blood vessel wall. During this procedure, fluoroscopic visualization methods can be used to determine if the implant is being positioned as desired.

If the positioning is as desired, the sheath is withdrawn along the entire length of the implant, thereby releasing the implant and allowing it to expand into contact with the blood vessel along the entire length of the implant. However, if it is determined prior to complete withdrawal of the sheath (and concurrent release of the implant) that the implant is not positioned exactly as desired, the sheath can be advanced to recapture the implant. Since, in each embodiment, the implant includes a connected anchor assembly along the entire length of the graft, compression of the trailing end of the graft, such as by advancing the sheath, allows the radial compression force to be communicated distally. As a result, the sheath may be advanced over the entire implant assembly, progressively collapsing and recapturing the implant.

Figure 10A:
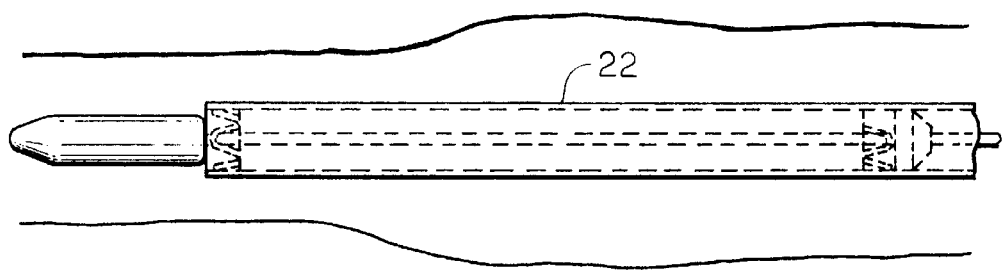
FIGS. 10A–10C are diagrammatic illustrations of the process by which an implant may be deployed without releasing the implant and in a manner that enables the implant to be recaptured for repositioning or removal.
Figure 10B:
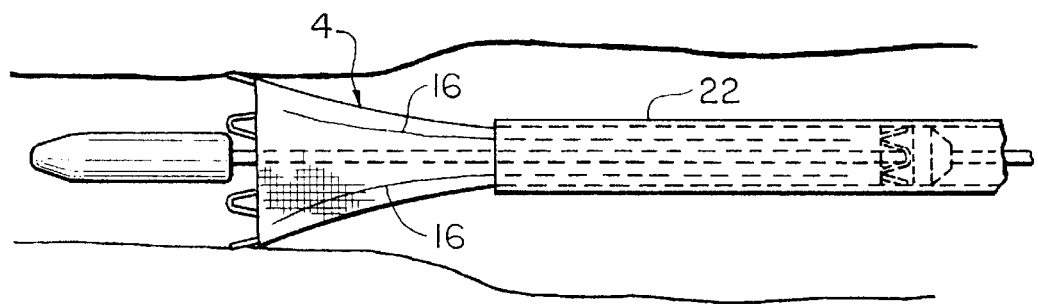
Figure 10C:
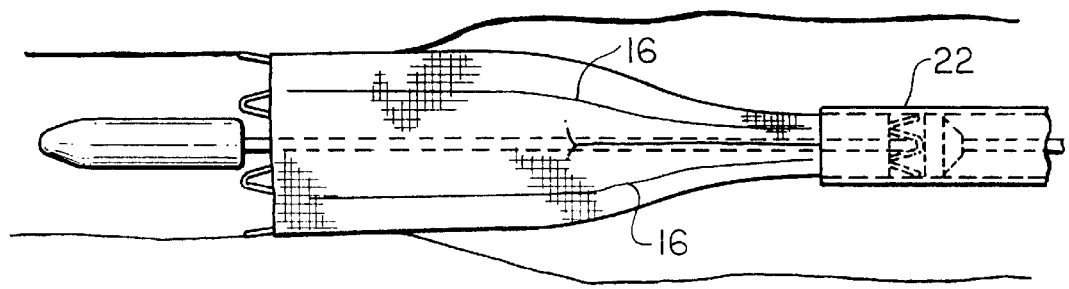

FIGS. 10A–10C depict the implant deployment process described above. FIG. 10A illustrates an implant 4 having anchors 10, 12 contained within the pod and disposed in an artery in readiness for deployment. FIG. 10B illustrates the device with the sheath withdrawn and with the leading anchor in engagement with the blood vessel. FIG. 10C illustrates a further stage of the deployment but with the trailing end of the implant maintained in engagement with the stay and retention device within the distal end of the pod. In the latter configuration, the leading end of the implant 4 has been deployed and has seated against the wall of the blood vessel. If at this point it is determined, such as by fluoroscopic visualization, that repositioning or removal of the implant is required, the sheath can be advanced distally to progressively recapture the implant. As shown in FIG. 10B, the sheath 22 can be advanced relative to the positioning tube 24 causing compression and recapture of a portion of the implant 4. The compression forces on the proximal end of the implant are transferred progressively to its distal end by the struts 16 causing the leading end of the implant 4 to begin contracting as well. In FIG. 10A, the sheath has been advanced over the entire length of the implant. In so doing, the implant has been removed from contact with the vessel wall and can be removed from the patient or positioned at a different location.

The control handle is associated with the sheath 22 and positioning tube 24 to perform several functions including (1) the advancement or withdrawal of the sheath 22 relative to the positioning tube 24 and implant assembly 4, (2) providing a means by which liquid can be delivered into and through the sheath 22 and (3) to limit the relative ranges of movement between the sheath and the positioning tube to prevent inadvertent, premature release of the implant assembly 4. The control handle is securely, but adjustably connectible to the positioning tube 24 to fix the positioning tube 24 relative to the handle. The trailing end of the sheath is contained within the control handle and is connected to a slide mechanism by which the sheath can be withdrawn or advanced relative to the handle and the positioning tube. The slide mechanism in the handle includes a gated slide arrangement by which the rearward movement of the slide is limited by a gating arrangement so that the sheath cannot be withdrawn sufficiently to completely release the implant assembly. In order to release the implant, the control handle must be operated in a manner that releases the slide to permit further rearward movement sufficient to uncover and completely release the trailing end of the anchor. The arrangement prevents continuous direct movement of the slide from the captured position to the release position and assures that the physician will have opportunity to evaluate the position and orientation of the partially deployed graft while avoiding inadvertent premature release.

The control handle 20 includes an elongate, generally tubular outer housing 50 that may be formed from a pair of molded components, including an upper housing portion 50a and a lower housing portion 50b. The housing portions 50a, 50b may be molded from any of a variety of suitable polymeric materials. Each of the upper and lower housing portions may be considered to include a central, longitudinally extending cylindrical portion 56a, 56b that, when the housing portions 50a, 50b are mated, define a generally circular cross-section. Each of the upper and lower housing portions 50a, 50b also includes a pair of opposed laterally projecting, longitudinally extending ribs that, when the portions 50a, 50b are assembled, will define side ribs 52 to facilitate gripping of the control handle 50 (FIG. 9A). The control handle thus has a greater widthwise dimension than heightwise, in cross-section. That configuration facilitates gripping of the device and also enables the physician to place the device against a supporting surface to help stabilize the device for operation with one hand.

The rear end of each of the housing portions 50a, 50b include end walls 66a, 66b. Each end wall 66a, 66b has a rearward extension that defines a collett finger 68A, 68B. The facing surfaces of each collett finger include grooves that, when the parts are mated, define a passage receptive to the rear portion of the positioning tube 24. The collett fingers 68a, 68b may be tightened about the positioning tube 24 by a nut 70 engageable with threads formed on the outer surface of the collett fingers 68a, 68b.

The upper housing portion includes an elongate slot 72 that provides access to the interior of the housing for a slide button by which a portion of the internal control mechanism is operated.

The outer housing 50 of the control handle contains a gating tube, indicated generally at 76 (FIG. 11). The gating tube 76 is rotatably contained within the cylindrical portions 56 of the outer housing 50. The gating tube 76 also may be formed from a pair of molded halves, 76a, 76b (FIG. 11). The halves 76a, 76b are formed so that when assembled, the leading end of the gating tube will include an integral knob 78 having an end wall 80 and an aperture 82 formed centrally in the end wall 80. The rear end of the gating tube 76 is open. The gating tube halves 76a, 76b, also are formed to include circumferential ribs 84, 86 that are receivable within arcuate slots 88, 90 formed in the upper and lower housing portions 50A, 50B (FIG. 11B). When the housing 50 and gating tube 76 are assembled, the gating tube 76 can be rotated within the housing 50 by manipulation of a knob 78. The halves 76a, 76b of the gating tube 76 also are formed so that when combined they will define a gating channel including two longitudinal, sequential slots 92, 94. The more forward slot 92 may have, at its forwardmost end, a circumferentially enlarged portion 96. A similarly circumferentially enlarged region 98 is formed at the transition between the forward slot 92 and the immediately adjacent rearward slot 94. The circumferentially enlarged slot portions 96, 98 define circumferential detent surfaces 100, 102, 104, 106.

A slide 108 is slidably contained within the gating tube 76. The slide 108 includes an upwardly projecting boss 110 that is connectible to a downwardly extending tongue 112 of the slide button 74. The boss 110 protrudes radially through one of the slots 92, 94 in the gating tube and into the slot 72 in the outer housing 50. The boss 110 and mated portion of the slide button 74 cooperatively extends through the slot 72 of the housing 50 and an aligned portion of the gating channel. The transition region 98 and detent surface 106 are disposed to limit rearward movement of the slide 108 to a position in which the retention device 36 remains within the pod. It will be appreciated, therefore, that the slide is permitted to move only within one of the slots 92, 94. Consequently, when the slide 108 has been retracted fully to the rear end of slot 92 and its boss 110 is engagement with the detent surface 106, further rearward movement of the slide 108 cannot occur until the gating tube 76 has been rotated to align the boss 110 with the slot 94. The circumferential extent of the transitional opening 98 is dimensioned to receive the boss 110 and permit such rotation.

Figure 13:
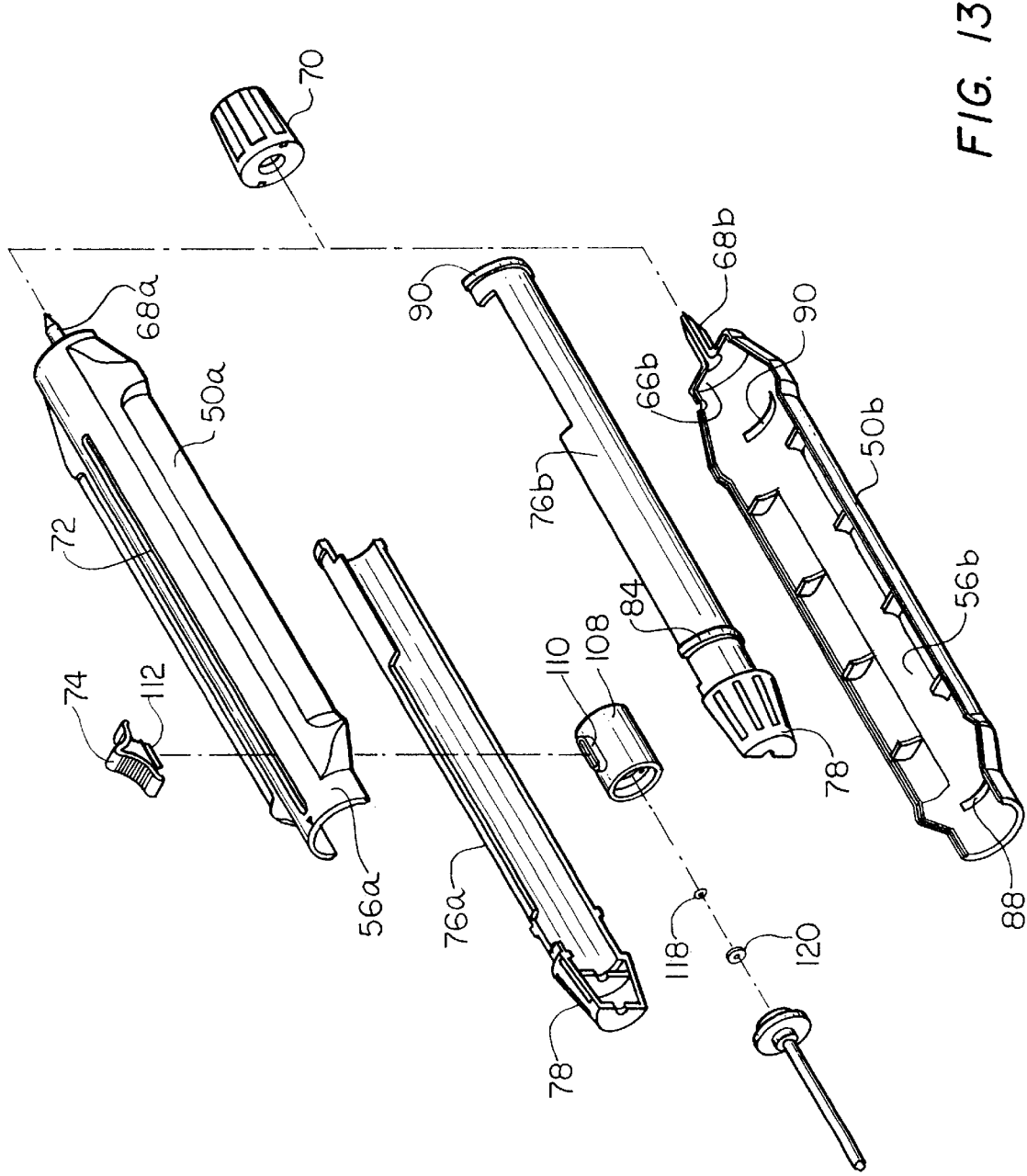
FIG. 13 is an exploded illustration of the handle and its internal components.
Figure 14:
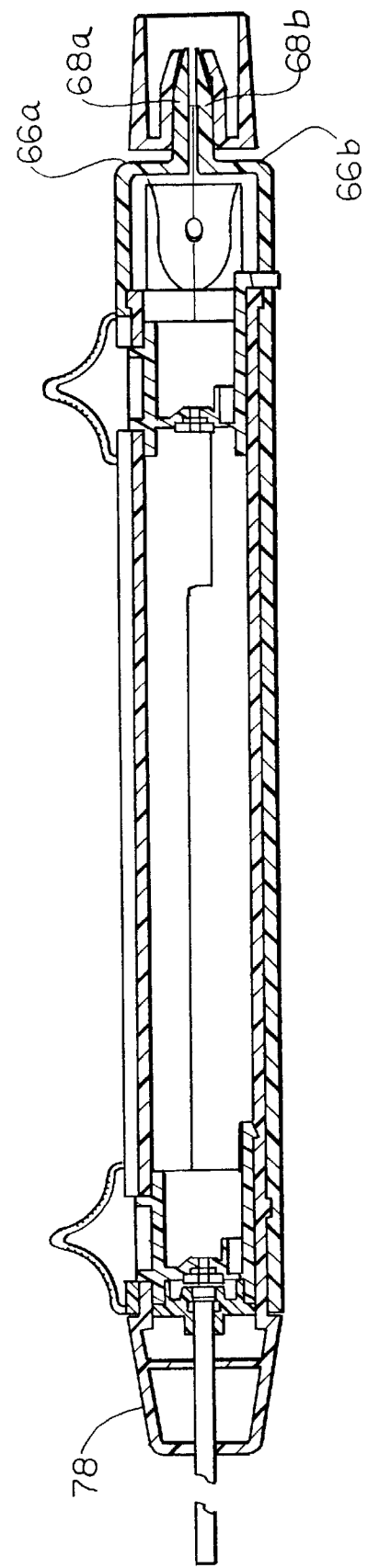
FIG. 14 is a longitudinal sectional illustration of the handle with several components omitted for clarity of illustration.
Figure 15:
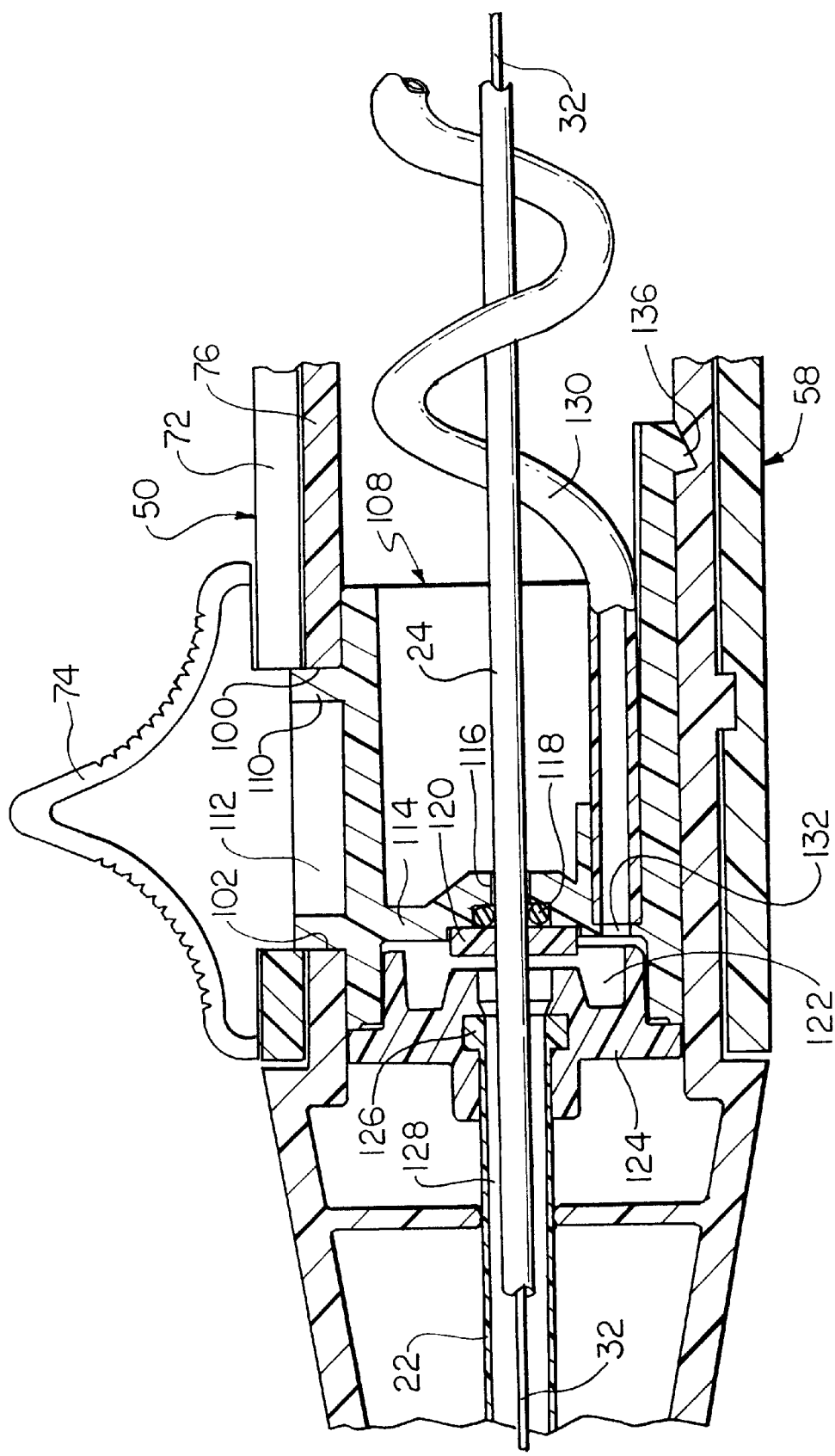
FIG. 15 is an enlarged sectional view of the connection between the distal end of the slide and its connection to the sheath of the delivery device.

The slide 108 is connected to the rear end of the sheath as illustrated in FIGS. 14 and 15. The device is constructed so that in addition to providing control over the extent to which the sheath is extended or withdrawn, means also is provided to enable liquid to be communicated to and through the sheath, for emission at the end of the pod. FIG. 13 shows the slide in its most forward position in which the boss 110 is disposed in the circumferentially enlarged portion 96 between detent surfaces 100, 102. In that configuration with the knob 78 having been rotated counterclockwise (as viewed from a rearward position and suggested by the arrow 79), the slide 108 is locked in that position, the boss 110 being captured between the detent surfaces 100, 102. In order to permit the slide 108 to be withdrawn rearwardly, the gating tube 76 must be rotated clockwise to align the boss 110 with the slot 92 in the gating tube 76.

As shown in detail in FIG. 15, the slide 108 includes an inner wall 114 with a central aperture 116 through which the positioning tube 24 extends. A liquid seal between the inner wall 114 and the positioning tube 24 is effected by an O-ring 118 contained in a recess in the front of the inner wall 114. The O-ring 118 is secured with respect to the inner wall 114 by a cap 120 secured to the front side of the inner wall 114 to capture the O-ring 118. The O-ring and positioning tube 24 are configured to enable the positioning tube 24 to slide freely within the O-ring 118 yet to maintain an effective liquid seal about the tube 24.

The portion of the slide 108 forward of the inner wall 114 defines a chamber 122 that may be enclosed by a front cap 124 attached, as by ultrasonic welding, to the front end of the slide 108. The cap has a central aperture. The sheath 22 extends through the aperture and is attached, at its rearward end, to the front cap 124 as by a circumferential flange 126 to assure a secure connection to the end cap 124. As shown, the positioning tube 24 extends through the central aperture of the end cap 124 and through the sheath 22. The outer diameter of the positioning tube 24 is less than the inner diameter of the sheath 22 to define an annular lumen 128 that extends all the way to the opening at the leading end of the pod. Thus, liquids can be injected through the lumen 128. The liquid is communicated to the chamber 122 and then to the lumen 128 by a flexible tube having a leading end connected to a port 132 in the inner wall 114 of the slide 108. The tube 130 may be helically coiled about the positioning tube 24 and emerges from the rear portion of the control handle. The tube 130 may be connected to a three-way stopcock 134, as described below. Liquid injected through the tube 130 thus will flow into the chamber 122 and then into the lumen 128 for delivery at the leading end of the device. The stay 28 is provided with holes through which the liquid may flow.

In operation, the device is loaded with the implant assembly by manipulating the controls to withdraw the sheath sufficiently rearwardly so that the stay 28 and anchor retainer 36 are exposed beyond the leading end of the pod 23. The longitudinal position of the support rod 24 is preliminarily set and secured relative to the control handle by tightening the nut about the collett at the rear end of the handle. The trailing end of the implant assembly then is engaged with the stay and retention device and the sheath is advanced to draw the implant assembly 4 into the pod 23. It may be desirable for the physician to assure that the control knob 78 has been rotated fully counterclockwise, indicated at arrow 79 to lock the slide button 74 within the region 96 of the gating tube 76. The device then may be advanced over a previously placed guidewire that serves to guide the device into the patient's vasculature. Should it be desired to replace the initial guidewire with a different guidewire (for example, a steerable guidewire) such a guidewire exchange can be performed through the positioning tube 24. With the guidewire having been advanced and manipulated to the intended deployment site, the delivery catheter than can be advanced over the guidewire. Should the physician desire to inject radiopaque contrast liquid at any time, a syringe with contrast liquid can be fitted to the stopcock 134 and injected into and through the annular lumen between the sheath 22 and the positioning rod 24. The sheath may be withdrawn slightly to facilitate flow of contrast liquid into the blood vessel.

When it has been determined that the implant is in the desired position and orientation for release, the control knob 78 is rotated to align the gating tube 76 to permit the slide to be withdrawn. The physician withdraws the sheath by operation of the slide button 74. At any time during the procedure additional contrast liquid may be injected. The slide 108 can only be withdrawn until it engages the detent surface 106. When setting up the device, the support tube 24 is secured in a position such that when the slide 108 has been brought to its pre-release position, in engagement with the detent surface 106, the stay 28 and retention device 36 will remain within the pod in engagement with the trailing end of the implant assembly. Only after the physician has determined that the device has been placed as desired, is the gating tube 76 rotated to permit further rearward advancement of the slide 108. When the slide has been drawn fully rearwardly, the stay 28 and retention device will be disposed outside of the pod 23 and the implant will have been released. If the physician determines, before release, that the position of the implant assembly is not as desired, the implant assembly can be recaptured as described above either to be repositioned or withdrawn.

The control handle may be provided with a detent 136 formed integrally with the slide (FIG. 15). The detent may be disposed so that when the slide has been brought fully rearwardly, it snaps into engagement with the free rear edge of the gating tube 76. The leading surface of the detent 136 may be formed at somewhat of an angle so that, if desired, the slide can be readvanced forwardly, but only under a substantial force that necessarily will be noticed by the physician.

From the foregoing, it will be appreciated that the invention provides an arrangement by which a tubular implant assembly may be advanced into a body lumen in a manner that reduces significantly the risk of the device being released prematurely before the position and orientation of the device has been verified. The device and method that it practices requires a deliberate manipulation on the part of the physician in order to release the device into the body lumen. In the event that the position is not as desired, the implant assembly can be easily recaptured for repositioning or withdrawal.

It should be understood that the foregoing description of the invention is intended merely to be illustrative thereof and that other embodiments, modifications and equivalents will be apparent to those skilled in the art without departing from its spirit.

Having thus described the invention what we desire to claim and secure by Letters Patent is:

1. A device for delivering, positioning and releasing, within a body lumen, a self-expandable implant comprising:
   an elongate tubular sheath for maintaining the implant in a low profile configuration, the sheath having a leading end and a trailing end and being open at its leading end;
   a control handle having a body and a movable portion, the movable portion being connected to a trailing portion of the sheath, the movable portion being movable along the body of the handle to effect forward and rearward motion of the sheath with respect to the body of the handle;
   an implant retainer engageable with the trailing end of the implant and being disposed to maintain the implant in a fixed position with respect to the body of the handle, the implant retainer being receivable within the sheath whereby the sheath may be moved between a forward, implant-capturing position in which the implant retainer is contained within the sheath and a rearward, implant-release position in which the implant retainer is disposed forwardly beyond the leading end of the sheath;
   the movable portion of the handle being movable between a forward implant-capturing position and a rearward implant release position, the implant retainer being constructed to engage the implant to enable the leading end of the implant to self-expand as the sheath is moved toward the implant-release position and;
   a detent carried by the handle to prevent continuous forward-rearward movement of the movable portion of the handle from the implant capture position to the implant release position.

2. A device as defined in claim 1 wherein the detent is manually releasable to free the movable portion of the handle for movement to a release position.

3. A device as defined in claim 2 wherein the detent is constructed so that it is movable to the release position only when the movable portion of the handle is disposed at the detent.

4. A device as defined in claim 1 further comprising a positioning tube extending through the sheath and the handle, the implant retainer being attached to the positioning tube.

5. A device as defined in claim 1 further comprising:
   the handle being elongate and hollow and having forward and rearward ends;
   the movable portion of the handle comprising a slide connected to the sheath, the slide being movable along the handle;
   the handle further having a gating mechanism engageable with the slide to confine movement of the slide to defined segments along the length of the handle, the gating mechanism having a position in which rearward movement of the slide is limited to a position between the capture and release positions;
   the gating mechanism being movably mounted to the handle to enable further rearward movement of the slide to the release position.

6. A device as defined in claim 5 further comprising:
   the slide being contained within the handle;
   the rear end of the sheath extending through the forward end of the handle and being connected to the slide within the handle.

7. A device as defined in claim 5 further comprising:
   the gating mechanism including a gate rotatable within the handle and including at least two elongate longitudinally extending sequential, circumferentially spaced slots;
   a control member disposed outside of the handle connected to the gate for effecting rotation of the gate.

8. A device as defined in claim 7 further comprising:
   the rotatable gate comprising a tubular member rotatable within the handle, the tubular member having a circumferential slot disposed at a juncture of the elongate slots, the slide having a portion thereof extendable through the elongate slots and the circumferential slot.

9. A device as defined in claim 8 further comprising:
   the forward-most end of the forward-most elongate slot having a circumferential slot engageable with the slide to enable locking the slide in a fully forward position.

10. A device as defined in claim 1 further comprising:
    the movable portion of the control handle having a fluid chamber in communication with the lumen of the sheath and an inlet port; and
    a conduit connected at one end to the inlet port and connectible at its other end to a fluid source.

11. A device as defined in claim 10 further comprising a positioning tube extending through the sheath and the handle, the positioning tube extending through the fluid chamber;
    a seal carried by the movable member and engageable with the positioning tube to effect a seal about the positioning tube.

12. A device as defined in claim 11 further comprising:
    a portion of the conduit being coiled about the positioning tube.

13. A device as defined in claim 1 further comprising:
    means for automatically locking the movable portion of the handle to a fixed portion of the handle when the handle has been withdrawn to the implant release position.

14. A device for delivering, positioning and releasing, within a body lumen, an expandable implant comprising:
    an elongate tubular sheath for maintaining the implant in a low profile configuration, the sheath having a leading end and a trailing end and being open at its leading end;
    a control handle having a movable portion thereof connected to a trailing portion of the sheath, the movable portion being movable along the handle to effect forward and rearward motion of the sheath with respect to the handle;
    an implant retainer engageable with the trailing end of the implant and being operatively associated with the handle to maintain the implant retainer in a fixed position with respect to the handle, the implant retainer being receivable within the sheath whereby the sheath may be moved between a forward implant capturing position in which the implant retainer is contained within the sheath and a rearward implant release position in which the implant retainer is disposed forwardly beyond the leading end of the sheath;
    the movable portion of the handle being movable between a forward implant-capturing configuration and a rearward implant release configuration;
    a positioning tube extending through the sheath and the handle, the implant retainer being attached to the positioning tube;

the positioning tube being movable along the longitudinal axis of the device; and a locking element carried by the handle for locking the positioning tube in a selected position with respect to the handle.

15. A device as defined in claim 14 wherein the locking element comprises a collett disposed at the rear end of the handle, the collett receiving the rearward portion of the positioning tube and a locking nut to releasably tighten the collett about the positioning tube.

16. A method for selectively delivering, positioning and releasing, within a body lumen, a self-expandable implant having leading and trailing ends comprising:

providing an elongate tubular sheath for maintaining the implant in a low profile configuration, the sheath having a leading end and a trailing end and being open at its leading end to receive the implant, an implant retainer engageable with the trailing end of the implant to retain the trailing end of the implant in a fixed position while enabling the sheath to be withdrawn rearwardly relative to the implant retainer and implant, the method further comprising:

inserting the sheath and implant retainer together with the implant contained within the sheath, into the body lumen and advancing them as a unit to a location in the body lumen;

providing a detent to prevent direct continuous movement of the sheath from a capture position to a release position;

withdrawing the sheath to the detent between the captured and release positions while exposing the leading end of the implant to enable the leading end of the implant to self-expand;

while in the detent configuration, determining whether the implant is in a desired position and orientation; and thereafter selectively (1) moving the detent to permit the sheath to be withdrawn to a release position or (2) without shifting the detent, returning the sheath to the capture position.

17. A device for delivering, positioning and releasing, within a body lumen, a self-expandable implant comprising:

an elongate tubular sheath for maintaining the implant in a low profile configuration, the sheath having a leading end and a trailing end and being open at its leading end;

a control handle having a body and a movable portion, the movable portion being connected to a trailing portion of the sheath, the movable portion being movable along the body of the handle to effect forward and rearward motion of the sheath with respect to the body of the handle;

means, engageable with the trailing end of the implant, for maintaining the implant in a fixed position with respect to the body of the handle, said means being receivable within the sheath whereby the sheath may be moved between a forward, implant-capturing position in which said means is contained within the sheath and a rearward, implant-release position in which said means is disposed forwardly beyond the leading end of the sheath;

the movable portion of the handle being movable between a forward implant-capturing position and a rearward implant release position, said means being constructed to engage the implant to enable the leading end of the implant to self-expand as the sheath is moved toward the implant-release position and;

a detent carded by the handle to prevent continuous forward-rearward movement of the movable portion of the handle from the implant capture position to the implant release position.

18. A device as defined in claim 17 wherein the detent is manually releasable to free the movable portion of the handle for movement to the release position.

19. A device as defined in claim 17 wherein the detent is constructed so that it is movable to the release position only when the movable portion of the handle is disposed at the detent.

20. A device as defined in claim 17 further comprising a positioning tube extending through the sheath and the handle, said means being attached to the positioning tube.

21. A device as defined in claim 17 further comprising:

the movable portion of the control handle having a fluid chamber in communication with the lumen of the sheath and an inlet port; and a conduit connected at one end to the inlet port and connectable at its other end to a fluid source.

22. A device as defined in claim 21 further comprising a positioning tube extending through the sheath and the handle, the positioning tube extending through the fluid chamber;

a seal carried by the movable member and engageable with the positioning tube to effect a seal about the positioning tube.

23. A device as defined in claim 17 further comprising:

means for automatically locking the movable portion of the handle to a fixed portion of the handle when the handle has been withdrawn to the implant release position.

24. A device for delivering, positioning and releasing, within a body lumen, an expandable implant comprising:

an elongate tubular sheath for maintaining the implant in a low profile configuration, the sheath having a leading end and a trailing end and being open at its leading end;

a control handle having a movable portion thereof connected to a trailing portion of the sheath, the movable portion being movable along the handle to effect forward and rearward motion of the sheath with respect to the handle;

means, engageable with the trailing end of the implant and being operatively associated with the handle, for maintaining the implant in a fixed position with respect to the handle, said means being receivable within the sheath whereby the sheath may be moved between a forward implant capturing position in which said means is contained within the sheath and a rearward implant release position in which said means is disposed forwardly beyond the leading end of the sheath;

the movable portion of the handle being movable between a forward implant-capturing position and a rearward implant release position;

a positioning tube extending through the sheath and the handle, said means being attached to the positioning tube;

the positioning tube being movable along the longitudinal axis of the device; and a locking element carried by the handle for locking the positioning tube in a selected position with respect to the handle.

25. A device as defined in claim 24 further comprising:

a slide being contained within the handle;

the trailing end of the sheath extending through the forward end of the handle and being connected to the slide within the handle.

26. A device as defined in claim 25 further comprising:
a gating mechanism including a gate rotatable within the handle and including at least two elongate longitudinally extending sequential, circumferentially spaced slots;
a control member disposed outside of the handle connected to the gate for effecting rotation of the gate.

27. A device as defined in claim 26 further comprising:
the rotatable gate comprising a tubular member rotatable within the handle, the tubular member having a circumferential slot disposed at a juncture of the elongate slots, the slide having a portion thereof extendable through the elongate slots and the circumferential slot.

28. A device as defined in claim 27 further comprising:
the forward-most end of the forward-most elongate slot having a circumferential slot engageable with the slide to enable locking the slide in a fully forward position.

29. A device as defined in claim 24 further comprising:
a portion of a conduit being coiled about the positioning tube.

30. A device as defined in claim 24 wherein the locking element comprises a collett disposed at the rear end of the handle, the collett receiving a rearward portion of the positioning tube and a locking nut to releasably tighten the collett about the positioning tube.

31. A device as defined in claim 1 further comprising:
the handle being elongate and hollow and having forward and rearward ends;
the movable portion of the handle comprising a slide connected to the sheath, the slide being movable along the handle;
the handle further having a gating mechanism engageable with the slide to confine movement of the slide to defined segments along the length of the handle, the gating mechanism having a position in which rearward movement of the slide is limited to a position between the capture and release positions;
the gating mechanism being movably mounted to the handle to enable further rearward movement of the slide to the release position.

* * * * *